United States Patent
Doerr

(10) Patent No.: US 8,538,518 B2
(45) Date of Patent: Sep. 17, 2013

(54) CARDIAC STIMULATOR FOR DELIVERY OF CARDIAC CONTRACTILITY MODULATION THERAPY

(75) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/494,988

(22) Filed: Jun. 12, 2012

(65) Prior Publication Data
US 2013/0006319 A1 Jan. 3, 2013

Related U.S. Application Data

(60) Provisional application No. 61/501,768, filed on Jun. 28, 2011.

(51) Int. Cl.
*A61N 1/365* (2006.01)
(52) U.S. Cl.
USPC .................................................. 607/4; 607/9
(58) Field of Classification Search
USPC ............................. 607/2–9, 14–18
See application file for complete search history.

(56) References Cited

U.S. PATENT DOCUMENTS

| 6,317,631 | B1 | 11/2001 | Ben-Haim et al. | |
|---|---|---|---|---|
| 2005/0080347 | A1* | 4/2005 | Sheth et al. | 600/515 |
| 2010/0069977 | A1 | 3/2010 | Stahamann | |
| 2010/0069980 | A1 | 3/2010 | Stahamann | |
| 2010/0069984 | A1 | 3/2010 | Stahamann | |
| 2010/0069985 | A1* | 3/2010 | Stahmann | 607/9 |

FOREIGN PATENT DOCUMENTS

| WO | 2007/029254 | 5/2007 |
|---|---|---|
| WO | 2007/091244 | 8/2007 |

OTHER PUBLICATIONS

European Search Report dated Apr. 25, 2013, 6 pages.

\* cited by examiner

*Primary Examiner* — Rex R Holmes
(74) *Attorney, Agent, or Firm* — ARC IP Law, PC; Joseph J. Mayo

(57) ABSTRACT

A combination cardiac stimulator for CRT stimulation and CCM stimulation, which is connected to a rhythm evaluation unit which can either detect a sinus rhythm that is present, or classify an atrial arrhythmia, and which comprises an additional therapy selection unit, wherein the therapy selection unit selects the delivery of either CRT therapy or CCM therapy on the basis of the classification of the atrial rhythm such that CRT therapy is preferred in the case of sinus rhythm, and CCM therapy is delivered in the case of atrial arrhythmia.

8 Claims, 3 Drawing Sheets

CARDIAC STIMULATOR FOR DELIVERY OF CARDIAC CONTRACTILITY MODULATION THERAPY

This application claims the benefit of U.S. Provisional Patent Application 61/501,768 filed on 28 Jun. 2011, the specification of which is hereby incorporated herein by reference.

BACKGROUND OF THE INVENTION

1. Field of the Invention

At least one embodiment of the invention relates to a cardiac stimulator for the delivery of cardiac therapy.

2. Description of the Related Art

Implantable cardiac stimulators in the form of cardiac pacemakers or cardioverters/defibrillators are typically connected to electrode leads which comprise stimulation electrodes and defibrillation electrodes—the latter of which may be provided in addition thereto, as an option—in a ventricle or in the immediate vicinity. Using a stimulation electrode, a cardiac pacemaker can deliver an electrical stimulation pulse to the muscle tissue of a ventricle to thereby induce a stimulated contraction of the ventricle provided the stimulation pulse has sufficient intensity and the cardiac muscle tissue (myocardium) is not in a refractory phase at the moment. Such a stimulated contraction of a ventricle is referred to as a stimulated event within the scope of this description. If a natural contraction of the ventricle occurs, this is referred to as natural action or a natural or intrinsic event within the scope of this description. A contraction of the right atrium of a heart, for instance, is referred to as an atrial event, which can be a natural atrial event, for instance, or—in the case of an atrial cardiac pacemaker—can also be a stimulated atrial event. In the same sense, a distinction can be made between natural (intrinsic) and stimulated left ventricular events and right ventricular events.

Local excitation of the myocardium propagates from the excitation site by conduction in the myocardium, resulting in depolarization of the muscle cells and thus contraction of the myocardium. After a brief period of time the muscle cells are repolarized and the myocardium therefore relaxes. During the phase of depolarization, the cardiac muscle cells are insensitive to excitation, i.e. they are refractory. This period is referred to as the refractory period. The electrical potentials associated with depolarization and repolarization can be sensed, and the variation thereof over time—referred to as an electrocardiogram—can be evaluated.

The cardiac rhythm of a healthy individual is determined by the sinoatrial node, which is controlled by the autonomic nervous system. It excites—via conduction—the right atrium of a human heart and furthermore, via the AV node, the (right) ventricle of the heart. A natural cardiac rhythm originating in the sinoatrial node is therefore also referred to as sinus rhythm and induces natural contractions of the particular ventricle, which can be detected as natural (intrinsic) events.

Such natural (intrinsic) events are detected by determining the electrical potentials of the myocardium of the particular ventricle using sensing electrodes, which are part of a corresponding electrode lead. The sensing electrodes can also be the stimulation electrodes, and can be used in alternation as stimulation electrodes and as sensing electrodes. Typically, a pair of sensing electrodes composed of two adjacent electrodes, i.e. a tip electrode and a ring electrode, is provided for the sensing, wherein the tip electrode is also used as the stimulation electrode. A bipolar recording of an intracardial electrocardiogram (IEGM) is obtained in this manner. In that case, sensing and stimulation take place in the ventricle using a ventricular electrode lead, and stimulation and sensing take place in the atrium (the right atrium) using an atrial electrode lead which is connected separately to the particular cardiac stimulator. In addition, a left ventricular electrode lead can be provided, which typically extends via the coronary sinus and a lateral vein branching off therefrom into the vicinity of the left ventricle, where it can comprise a stimulation electrode and/or sensing electrode having a small surface area.

During operation of the cardiac stimulator, the sensing electrodes are connected to appropriate sensing units which are designed to evaluate a particular electrocardiogram recorded using a sensing electrode (or a pair of sensing electrodes), and, in particular, to detect intrinsic atrial or ventricular events, i.e. natural atrial or ventricular contractions. This takes place, for example, by comparison with a threshold value, i.e. an intrinsic event is detected when a particular intracardial electrocardiogram exceeds a suitably specified threshold value.

On the basis of the frequency at which the atrial and ventricular events follow one another, the particular intrinsic atrial heart rate (atrial frequency) or ventricular heart rate (ventricular frequency) can be derived, thus enabling detection of tachycardias, for example.

In the case of known demand pacemakers, the detection of natural events is also used to suppress (inhibit) the delivery of stimulation pulses to a particular ventricle if the natural event is detected within a time window before the planned delivery of a stimulation pulse to the ventricle. In the case of rate-adaptive cardiac pacemakers, the point in time for delivery of a particular stimulation pulse is planned depending on a particular stimulation rate, which should correspond to a patient's physiological demand, and is higher when exertion is greater, for instance. For this purpose, a cardiac stimulator can be equipped with one or more activity sensors, which can be a CLS sensor, for instance, which is described in greater detail below.

The natural effect of the autonomic nervous system on the heart rate, which is simulated by a rate-adaptive cardiact stimulator, is referred to as chronotropism.

Cardiac performance is determined by chronotropism as well as contractility, the influencing of which is referred to as inotropism.

To determine the contractility of a heart, it is known to install an impedance or conductivity meter in a housing of a cardiac stimulator (e.g. an implantable cardiac pacemaker), which is designed to generate a unipolar or bipolar signal indicating the variation of impedance or conductivity. For this purpose, a plurality of impedance or conductivity values or a related variation in impedance or conductivity can be measured during at least one cardiac cycle. This takes place either in a unipolar manner by performing a measurement between a neutral electrode and a measuring electrode, or between two measuring electrodes. In addition, an evaluation unit is disposed in the housing, which is used to evaluate the variation in impedance or conductivity, and to determine a contractility value on the basis of the variation in impedance or conductivity. Electrotherapeutic devices that can determine the contractility of a heart can be used to adapt a therapy to be delivered by the electrotherapy device to the particular contractility state of the patient's heart.

As indicated, contractility describes an inotropic state of a heart. Contractility influences the force and speed of a myocardial contraction. Contractility is controlled by three mechanisms:
  direct control by the autonomic nervous system (ANS),
  the so-called Starling mechanism, and the so-called Bowditch effect (force-frequency coupling).

The main mechanism, the control of circulatory regulation by the autonomic nervous system, increases contractility and heart rate when metabolic demand is elevated e.g. during physical or mental exertion, to ensure suitable blood supply. In a healthy individual, the inotropism of the heart therefore causes contractility to increase due to increased physiological demand.

In patients with chronic heart failure (CHF), myocardial contractility decreases to a low level, and interventricular synchronization is worsened. This is accompanied by a low ejection fraction (EF), and by a low quality of life and high mortality. HF occurs frequently in the population. Recently, HF patients have been treated with resynchronization therapy devices, such as 3-chamber cardiac pacemakers or defibrillators. The objective of such pacemaker therapy is to synchronize the two ventricles of a heart using biventricular stimulation in order to improve the time behavior of the ventricles and, therefore, cardiac performance. Such therapy is also referred to as cardiac resynchronization therapy (CRT). Cardiac resynchronization therapy (CRT) is adequately known.

Since the contractility of the heart is controlled physiologically by the autonomic nervous system, the detection of contractility can also be utilized to adjust a physiologically adequate stimulation rate in the case of rate-adaptive cardiac pacemakers. This type of stimulation rate control, which was addressed above, is also known as closed loop stimulation (CLS).

For CLS, the intracardial variation in impedance is measured after the onset of ventricular contraction. The measurement is performed for intrinsic events and stimulated events. There is a direct dependence between the right-ventricular variation in impedance and contraction dynamics. In turn, contraction dynamics are a parameter for stimulation of the heart by the sympathetic nervous system.

As stated, closed loop stimulation is used to control the stimulation rate in the case of a rate-adaptive cardiac pacemaker.

It is known to use cardiac contractility modulation (CCM) to increase the contractility of a ventricle.

Systems for CCM therapy are known from publications such as US 2010/0069977 A1, US 2010/0069980 A1, US 2010/0069984 A1 and US 2010/0069985 A1. A system such these comprises a stimulation pulse generator which is connected to three electrodes, one of which is disposed in the atrium and two of which are disposed at the septum of the right ventricle of a patient during operation. The therapeutic principle is based on delivery of biphasic stimulation pulses with an amplitude of 7-10V and a total pulse duration of ~20 ms in the absolute refractory period of the ventricle, with the objective of increasing contractility. The therapy is delivered for certain units of time throughout the day (e.g. 1 h on, 1 h off).

The principle of cardiac contractility modulation therapy is also described, inter alia, in U.S. Pat. No. 6,317,631 B1.

The effect of CCM therapy is based—according to current speculation—on a modification of cellular calcium ion exchange and therefore results in increased contraction force, which should also deliver a therapeutic benefit if atrial fibrillation is present. Although this has not been proven clinically, it can be explained pathophysiologically.

US 2010/0069977 A1, US 2010/0069980 A1, US 2010/0069984 A1, US 2010/0069985 A1 describe methods for delivering CCM stimulation on demand. The documents provide general descriptions of the use of physiological sensors, renal or cardiac function sensors, electrolyte sensors, serum sensors (e.g. creatinine), neurosensors (vagus nerve, sympathetic nervous system), adverse event detectors, worsening heart failure sensors, MRT sensors, activity sensors, sleep apnea sensors, ischemia sensors, sensors for metabolic demand and infarct sensors, and CCM controls that are dependent on cardiac rhythm. The stated prior art also describes a disabling of the CCM therapy when atrial fibrillation or atrial arrhythmia is detected (see US 2010/0069977 FIG. 20A and [0332]). It also provides a general description of the possible combination of CCM with other forms of stimulation and electrotherapy, such as CRT, ICD and neurostimulation.

BRIEF SUMMARY OF THE INVENTION

The problem addressed by at least one embodiment of the invention is that of creating an improved cardiac stimulator.

This problem is solved according to at least one embodiment of the invention by a cardiac stimulator having the following components:
at least one stimulation unit which is connected or connectable to one or more stimulation electrodes, and is designed to generate—in response to a related trigger signal—stimulation pulses to be delivered via at least one stimulation electrode, and
a cardiac rhythm detection unit which is designed to detect at least one atrial cardiac rhythm, and
a control unit which is connected to the stimulation unit and the cardiac rhythm detection unit, and is designed to control delivery of a stimulation pulse via the stimulation unit such that the cardiac stimulator can deliver above-threshold stimulation pulses to stimulate contraction of a ventricle, and sub-threshold stimulation pulses for cardiac contraction modulation therapy.

According to at least one embodiment of the invention, the control unit is designed to control a stimulation unit—in response to detection of atrial arrhythmia by the cardiac rhythm detection unit—such that it can generate and deliver sub-threshold stimulation pulses for cardiac contractility modulation therapy within the scope of cardiac contractility modulation therapy and, in response to detection of a sinus rhythm by the cardiac rhythm detection unit, to control the stimulation unit such that it can deliver—on demand, at least—above-threshold stimulation pulses to stimulate contraction of a ventricle, but not sub-threshold stimulation pulses for cardiac contraction modulation therapy.

In other words, the problem is solved by a combination cardiac stimulator for CRT stimulation and CCM stimulation, which is connected to a rhythm evaluation unit which can either detect a sinus rhythm that is present, or classify an atrial arrhythmia, and which comprises an additional therapy selection unit, wherein the therapy selection unit selects the delivery of either CRT therapy or CCM therapy on the basis of the classification of the atrial rhythm such that CRT therapy is preferred in the case of sinus rhythm, and CCM therapy is delivered in the case of atrial arrhythmia.

Said cardiac stimulator is therefore a device for the combined use of cardiac resynchronization therapy (CRT) and cardiac contractility modulation (CCM) in an electronic implant.

The cardiac stimulator is capable of selecting the particular form of therapy such that the therapy that provides the greatest therapeutic benefit to the patient at the moment is always activated. The cardiac stimulator is therefore capable of combining cardiac contractility modulation (CCM) therapy and cardiac resynchronization therapy (CRT) such that the result is a maximum expected clinical benefit to the patient by always applying the particular therapy that is the superior therapy concept.

The cardiac stimulator according to the invention offers the advantage that the most effective therapy for a particular case is selected automatically depending on the rhythm state of a patient with cardiac insufficiency, thereby increasing the effectiveness of therapy. The advantages of CCM therapy and CRT are therefore combined in one device.

At least one embodiment of the invention makes use of the finding in US 2010/0069977 A1, US 2010/0069980 A1, US 2010/0069984 A1, US 2010/0069985 A1 that describe a disabling of CCM therapy when atrial fibrillation or atrial arrhythmias are detected. However, these documents do not address the reason why CCM is disabled. One speculation is that it may not be possible to synchronize CCM therapy correctly in the presence of atrial arrhythmias. This cannot be demonstrated, however, in the case of CCM timing that is linked to the ventricular event.

However, since CCM therapy is the preferred therapeutic option for so-called CRT non-responders, and atrial arrythmia is one of the known causes for a CRT non-response, the invention has uncovered a promising approach of activating CCM therapy precisely in the presence of atrial arrhythmias.

Although documents US 2010/0069977 A1, US 2010/0069980 A1, US 2010/0069984 A1, US 2010/0069985 A1 also describe the possible combination of CCM and CRT stimulation in one device, they do not specifically address the possibility of switching between CCM and CRT stimulation. They merely consider a different stimulation threshold for CRT stimulation and CCM.

The cardiac stimulator presented here is based on the assumption that CRT stimulation is clearly superior to CCM therapy in terms of the therapeutic benefit for cases of sinus rhythm. In cases of atrial arrhythmias, in particular atrial fibrillation, however, CCM therapy is more effective than CRT stimulation, at least in selected patients. The background is that CRT stimulation induces a mechanical resynchronization of the heart, although the benefit was demonstrated only when the interventricular resynchronization was accompanied by adequate atrio-ventricular synchronization. Otherwise, the positive effect of CRT stimulation is more than offset by the absence of AV synchronization.

Preferably, the cardiac rhythm detection unit comprises an atrial rhythm evaluation unit, which is connected to an atrial electrode configured for placement in the right atrium of a heart.

Preferably, the cardiac rhythm detection unit and, if applicable, the atrial rhythm evaluation unit thereof, are designed to evaluate the frequency and stability of a ventricular rhythm in order to diagnose atrial fibrillation.

Preferably, the cardiac stimulator is an implantable cardioverter/defibrillator (ICD) and/or a biventricular cardiac pacemaker (CRT-D) and/or a neurostimulator.

Preferably, the control unit is configured such that the cardiac contractility modulation therapy (CCM therapy) is controlled, in addition, by a further sensor (activity, metabolic demand, closed loop stimulation (CLS), ventricular potential, renal function sensor, pulmonary function sensor, cardiac function sensor, electrolyte sensor, neurosensor/vagus nerve/sympathetic nervous system, adverse event sensor, worsening heart failure sensor, sleep apnea sensor, ischemia sensor, infarct sensor, etc.).

Preferably, the cardiac stimulator is simultaneously an implantable cardioverter for the electrical conversion of atrial fibrillation, wherein the control unit is configured such that a defined phase of CCM therapy always precedes a cardioversion attempt for atrial fibrillation in order to improve the success of cardioversion. Such a preferred cardiac stimulator is used with the aim of normalizing the left-atrial pressure conditions using CCM therapy before cardioversion takes place.

To solve the problem, a method for the therapy of a heart is also provided, in which either cardiac contractility modulation therapy (CCM) or cardiac resynchronization therapy (CRT) is delivered, and cardiac contractility modulation therapy is delivered when atrial arrhythmia is present, and cardiac resynchronization therapy is delivered when atrial arrhythmia is not present.

A variant of the method relates to an operating procedure for a related cardiac stimulator for non-therapeutic purposes as well.

BRIEF DESCRIPTION OF THE DRAWINGS

At least one embodiment of the invention will now be explained in greater detail with reference to the drawings. In the drawings.

DETAILED DESCRIPTION

Figure 1:
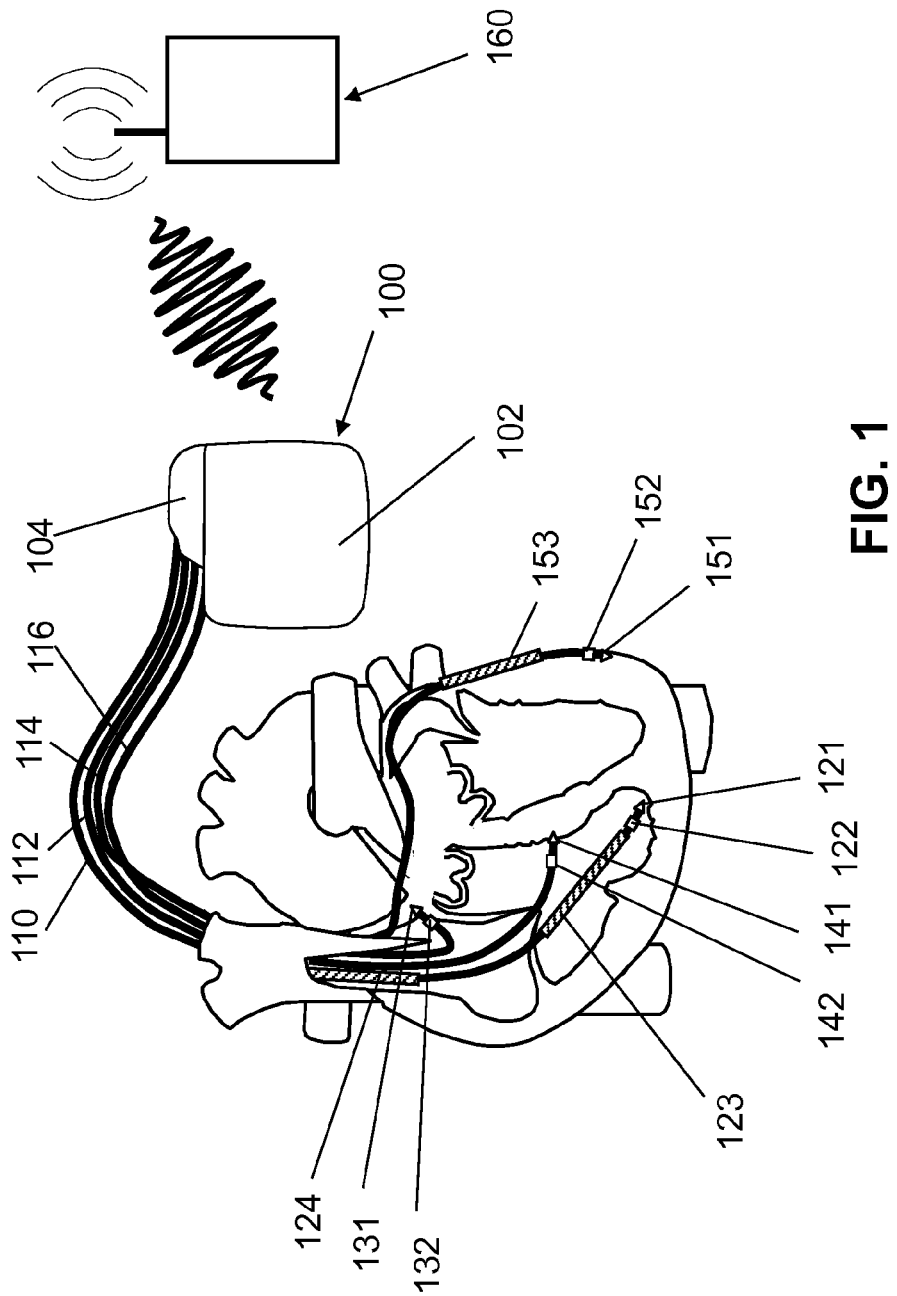
FIG. 1 shows a cardiac stimulator as CRT-CCM stimulator.

FIG. 1 shows, as an example of implementation, a three-chamber ICD system having a switchable CRT-CCM function. The cardiac stimulator (pulse generator or a simple generator) 100 is connected to a plurality of implantable electrode leads 110, 112, 114 and 116. Generator 100 comprises a housing 102 which, in this example, is composed of metal and is therefore electrically conductive, and is hermetically sealed housing 102 contains electronic and electrical components of generator 100, such as a battery, control electronics, stimulation pulse generators, sensing units comprising appropriate amplification and filter electronics. Said components are detachably connected to electrode leads 110, 112, 114 and 116 via electrical plug connectors in a connector housing 104 (which is also referred to as a header).

For purposes of right-ventricular sensing and stimulation, right-ventricular electrode lead 110 comprises a right-ventricular tip electrode 121 and a right-ventricular ring electrode 122 on the distal end. The right-ventricular stimulation pulses for biventricular CRT stimulation are delivered via right-ventricular tip electrode 121. A distal shock coil 123 and, optionally, a proximal shock coil 124 are installed on said right-ventricular electrode lead 110 to deliver a defibrillation shock. Generator housing 100 is the counterelectrode in this case.

Right-atrial electrode lead 116 comprises, on distal end thereof, a bipolar sensing and stimulation pole (comprising a right-atrial tip electrode 131 and a right-atrial ring electrode 132), and is used to sense the atrial rhythm, and for atrial stimulation as necessary.

For CCM stimulation—i.e. cardiac contractility modulation therapy—one or more right-ventricular septal electrode leads 112 deliver CCM pulses to the ventricular septum via a tip electrode 141 and ring electrode 142.

The system also comprises a left-ventricular or CS (coronary sinus) electrode lead 114 for delivery of left-ventricular stimulation pulses for CRT via a left-ventricular tip electrode 151 and a left-ventricular ring electrode 152. A left-ventricular shock coil 153 is provided as an option to ensure more effective defibrillation/cardioversion.

Communication with external devices 160 for programming, control, and data transmission takes place via a wireless, bidirectional telemetry unit.

Figure 2:
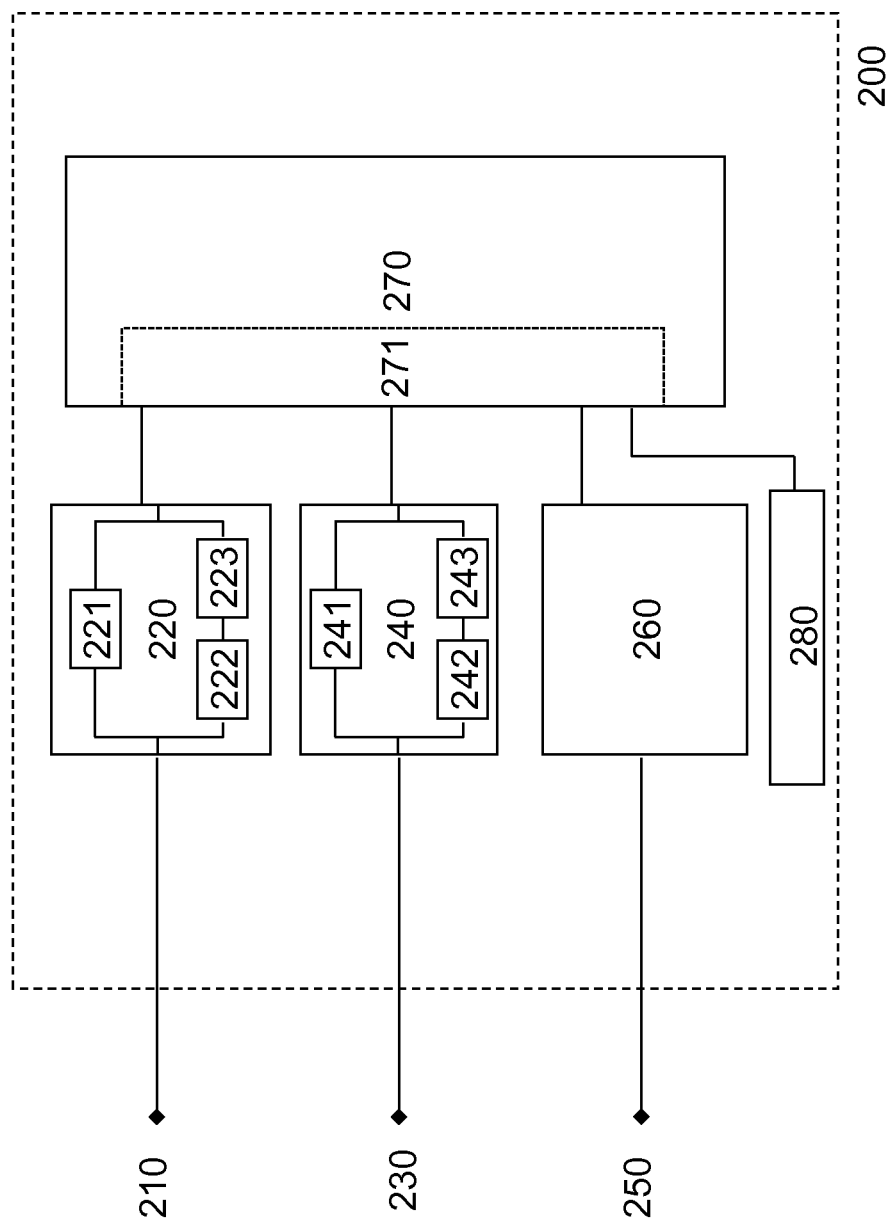
FIG. 2 shows a block diagram of main components of the cardiac stimulator.

FIG. 2 shows a schematic block diagram of a combination CRT-CCM stimulator. It comprises the following components, at the least: Generator 200; right-atrial electrode 210 connected to an atrial sensing and stimulation unit 220 for classification of the atrial rhythm and on-demand atrial stimulation; right- and left-ventricular electrode connectors 230, connected to a biventricular sensing and stimulation unit 240 for sensing and classifying the ventricular rhythm and for biventricular CRT stimulation, and one or more CCM electrodes 250 connected to a CCM stimulation unit 260, wherein atrial sensing and stimulation unit 220, biventricular sensing and stimulation unit 240, and CCM stimulation unit 260 are connected to a control unit 270. Control unit 270 contains a therapy selection unit 271. Therapy selection unit 271 activates either biventricular stimulation unit 240 or CCM stimulation unit 260, depending on the classification of the atrial rhythm.

Biventricular sensing and stimulation unit 240 comprises a ventricular stimulation unit 241, which is known per se, and sensing unit 242. Biventricular sensing and stimulation unit 240 also comprises a ventricular rhythm evaluation unit 243.

Atrial sensing and stimulation unit 220 is designed to classify the atrial rhythm and perform on-demand atrial stimulation of the atrium, and comprises atrial stimulation unit 221 and sensing unit 222, which are known per se. Atrial sensing and stimulation unit 220 also contains an atrial rhythm evaluation unit 223 which classifies the atrial rhythm in a manner known per se, and which is capable of detecting atrial fibrillations and distinguishing same from non-pathological atrial rhythms by analysis of the atrial heart rate, for example. The output signal of atrial rhythm evaluation unit 223 is supplied to therapy selection unit 271.

A hemodynamic or activity sensor 280 delivers an output signal during operation, which reflects a patient's metabolic demand and can likewise be evaluated by therapy selection unit 271.

Figure 3:
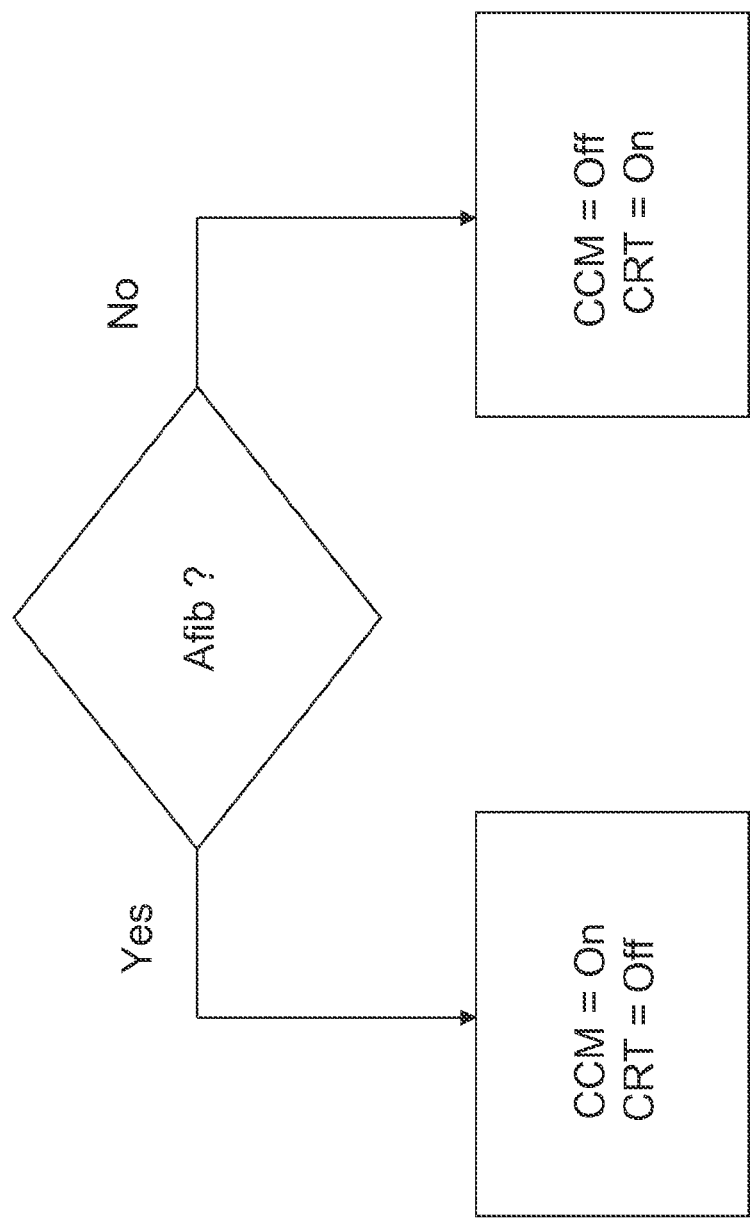
FIG. 3 shows a flow chart for therapy selection.

The mode of operation of therapy selection unit 271 is shown in FIG. 3 in the form of a flow chart for therapy selection. If atrial rhythm evaluation unit 223 detects an atrial fibrillation or atrial arrhythmia (Afib), therapy selection unit 271 enables CCM stimulation and disables biventricular stimulation. If there is no atrial fibrillation present, therapy selection unit 271 disables CCM stimulation and enables biventricular stimulation.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A cardiac stimulator configured to deliver cardiac resynchronization therapy or CRT stimulation and cardiac contractility modulation therapy or CCM stimulation comprising:
at least one stimulation unit configured to connect to one or more stimulation electrodes, and which is further configured to generate stimulation pulses to be delivered via at least one stimulation electrode in response to a related trigger signal;
a cardiac rhythm detection unit configured to detect at least one atrial cardiac rhythm; and,
a control unit connected to the at least one stimulation unit and the cardiac rhythm detection unit, and which is configured to
control a delivery of a stimulation pulse via the at least one stimulation unit such that the cardiac stimulator is configured to deliver above-threshold stimulation pulses to stimulate contraction of a ventricle, and to deliver sub-threshold stimulation pulses for cardiac contraction modulation therapy; and
control the at least one stimulation unit in response to detection of atrial cardiac arrhythmia by the cardiac rhythm detection unit, to deliver said sub-threshold stimulation pulses for the cardiac contraction modulation therapy and, in response to detection of a sinus rhythm by the cardiac rhythm detection unit, control the at least one stimulation unit to deliver said above-threshold stimulation pulses to stimulate a contraction of the ventricle, but not sub-threshold pulses for the cardiac contraction modulation therapy;
wherein the cardiac rhythm detection unit can either detect a sinus rhythm that is present, or classify an atrial arrhythmia, and which comprises a therapy selection unit, wherein the therapy selection unit selects the delivery of either CRT stimulation or CCM stimulation based on classification of atrial rhythm such that CRT stimulation is delivered in the case of the sinus rhythm, and CCM stimulation is delivered in the case of the atrial cardiac arrhythmia.

2. The cardiac stimulator according to claim 1, wherein the cardiac rhythm detection unit comprises an atrial rhythm evaluation unit configured to connect to an atrial electrode configured for placement in a right atrium of a heart.

3. The cardiac stimulator according to claim 2, wherein the cardiac rhythm detection unit or the atrial rhythm evaluation unit assigned thereto are configured to evaluate a frequency and stability of a ventricular rhythm in order to diagnose atrial fibrillation.

4. The cardiac stimulator according to claim 1, wherein the cardiac stimulator is an implantable cardioverter/defibrillator (ICD) and/or a biventricular cardiac pacemaker (CRT-D) and/or a neurostimulator.

5. The cardiac stimulator according to claim 4, wherein the cardiac stimulator is simultaneously an implantable cardioverter for electrical conversion of atrial fibrillation, wherein the control unit is configured such that a defined phase of CCM or Cardiac Contractility Modulation therapy always precedes a cardioversion attempt in response to atrial fibrillation in order to improve a success of cardioversion.

6. The cardiac stimulator according to claim 1, wherein the cardiac stimulator further comprises a sensor configured to deliver an output signal that reflects an acitivity, metabolic demand, and/or ventricular potential, or is a renal function sensor, pulmonary function sensor, cardiac function sensor, electrolyte sensor, neurosensor/vagus nerve/sympathetic nervous system, adverse event sensor, worsening heart failure sensor, sleep apnea sensor, ischemia sensor or infarct sensor, and is connected to the control unit, wherein the control unit is configured to evaluate the output signal of said sensor and to control the cardiac contraction modulation therapy.

7. A method for the therapy of a heart using the cardiac stimulator of claim 1, in which either cardiac contractility modulation therapy or CCM stimulation or cardiac resynchronization therapy or CRT stimulation is delivered comprising:
delivering the cardiac contractility modulation therapy when atrial arrhythmia is present, and delivering cardiac resynchronization therapy when atrial arrhythmia is not present.

8. The cardiac stimulator according to claim 2, wherein the atrial rhythm evaluation unit is configured to generate an output signal of an atrial rhythm, wherein the output signal is suplied to the therapy selection unit.

\* \* \* \* \*